US007106055B2

(12) United States Patent  (10) Patent No.: US 7,106,055 B2
Goldfine et al.  (45) Date of Patent: Sep. 12, 2006

(54) FABRICATION OF SAMPLES HAVING PREDETERMINED MATERIAL CONDITIONS

(75) Inventors: Neil J. Goldfine, Newton, MA (US); Vladimir A. Zilberstein, Chestnut Hill, MA (US); David C. Grundy, Reading, MA (US); Volker Weiss, Syracuse, NY (US); Andrew P. Washabaugh, Chula Vista, CA (US)

(73) Assignee: Jentek Sensors, Inc., Waltham, MA (US)

( * ) Notice: Subject to any disclaimer, the term of this patent is extended or adjusted under 35 U.S.C. 154(b) by 124 days.

(21) Appl. No.: 10/989,115

(22) Filed: Nov. 15, 2004

(65) Prior Publication Data

US 2005/0146324 A1    Jul. 7, 2005

Related U.S. Application Data

(60) Provisional application No. 60/520,000, filed on Nov. 14, 2003, provisional application No. 60/569,216, filed on May 7, 2004.

(51) Int. Cl.
*G01N 27/82* (2006.01)

(52) U.S. Cl. .................. 324/238; 324/240; 324/209; 324/226

(58) Field of Classification Search ............. 324/209, 324/228–243, 226; 29/592–595
See application file for complete search history.

(56) References Cited

U.S. PATENT DOCUMENTS

| 4,814,690 | A | 3/1989 | Melcher et al. |
|---|---|---|---|
| 5,015,951 | A | 5/1991 | Melcher |
| 5,227,731 | A * | 7/1993 | Prabhakaran et al. ....... 324/718 |
| 5,453,689 | A | 9/1995 | Goldfine et al. |
| 5,793,206 | A | 8/1998 | Goldfine et al. |
| RE36,986 | E | 12/2000 | Melcher |
| 6,188,218 | B1 | 2/2001 | Goldfine et al. |
| 6,380,747 | B1 | 4/2002 | Goldfine et al. |
| 6,486,673 | B1 | 11/2002 | Goldfine et al. |
| 6,657,429 | B1 | 12/2003 | Goldfine et al. |
| 6,727,690 | B1 * | 4/2004 | Soules ....................... 324/209 |
| 6,781,387 | B1 | 8/2004 | Goldfine et al. |
| 6,784,662 | B1 | 8/2004 | Schlicker et al. |
| 2002/0075006 | A1 | 6/2002 | Goldfine et al. |
| 2002/0158626 | A1 | 10/2002 | Shay et al. |
| 2002/0163333 | A1 | 11/2002 | Schlicker et al. |

OTHER PUBLICATIONS

Auld, B.A. and Moulder, J.C. (1999), "Review of Advances in Quantitative Eddy-Current Nondestructive Evaluation," *Journal of Nondestructive Evaluation*, vol. 18, No. 1.

* cited by examiner

*Primary Examiner*—Jay M. Patidar
(74) *Attorney, Agent, or Firm*—Hamilton, Brook, Smith, & Reynolds, P.C.

(57) ABSTRACT

Fabrication of samples having material conditions or damage representative of actual components inspected by nondestructive testing involves sensors placed near or mounted on the material surface, such as flexible eddy current sensors or sensor arrays, to monitor the material condition while the sample is being processed. These sample typically have real cracks in or around holes, on curved surfaces, in and under coatings, and on shot peened or otherwise preconditioned surfaces. Processing, such as mechanical or thermal loading to introduce fatigue damage, is stopped once the material condition reaches a predetermined level.

40 Claims, 16 Drawing Sheets

FABRICATION OF SAMPLES HAVING PREDETERMINED MATERIAL CONDITIONS

RELATED APPLICATION(S)

This application claims the benefit of U.S. Provisional Application Nos. 60/520,000, filed Nov. 14, 2003, and 60/569,216, filed May 7, 2004. The entire teachings of the above applications are incorporated herein by reference.

GOVERNMENT SUPPORT

The invention was supported, in whole or in part, by a Contract Number F09650-02-C-0516 from the Department of the Air Force and by Contract Number N68335-03-C-0123 from the Department of the Navy. The Government has certain rights in the invention.

BACKGROUND OF THE INVENTION

This application addresses nondestructive materials characterization and, particularly fabrication of reference samples for validating inspection methods and for establishing correlations between sensor responses and actual material condition. The nondestructive material characterization provides a quantitative, model-based characterization of surface, near-surface, and bulk material condition for flat and curved parts or components using magnetic field based or eddy-current sensors. Characterization of bulk material condition includes (1) measurement of changes in material state, i.e., degradation/damage caused by fatigue damage, creep damage, thermal exposure, or plastic deformation; (2) assessment of residual stresses and applied loads; and (3) assessment of processing-related conditions, for example from aggressive grinding, shot peening, roll burnishing, thermal-spray coating, welding or heat treatment. It also includes measurements characterizing material, such as alloy type, and material states, such as porosity and temperature. Characterization of surface and near-surface conditions includes measurements of surface roughness, displacement or changes in relative position, coating thickness, temperature and coating condition. Each of these includes detection of electromagnetic property changes associated with either microstructural and/or compositional changes, or electronic structure (e.g., Fermi surface) or magnetic structure (e.g., domain orientation) changes, or with single or multiple cracks, cracks or stress variations in magnitude, orientation or distribution.

Conventional eddy-current sensing involves the excitation of a conducting winding, the primary, with an electric current source of the prescribed frequency. This excitation produces a time-varying magnetic field, which in turn is detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the test material can be deduced from measurements of the impedance between the primary and secondary windings. Scanning of eddy-current sensors across the material surface is then traditionally used to detect flaws, such as cracks.

For fatigue inspection applications where cracks need to be detected and/or sized, typical nondestructive evaluation (NDE) or inspection (NDI) methods use reference standards or samples based on EDM notches. Some standards have only the notches themselves while other standards have fatigue cracks grown from EDM notches with the original notch removed, such as the engine structural integrity program (ENSIP) standards. However, there can be differences in morphology, shape, and distribution compared to cracks grown under service conditions so that they may not be sufficient to demonstrate detection reliability for relatively small crack sizes in engine or structural components. This is especially true for shot peened or otherwise cold worked surfaces, where creating the EDM notch itself can significantly alter the material properties, such as the residual stress distribution in a cold worked surface.

SUMMARY OF THE INVENTION

This application addresses the need for creation of NDI samples and reference specimens with real cracks for real surface conditions and non-flat material geometries. Aspects of the invention described herein involve nondestructive condition monitoring of materials and the creation of samples having a predetermined material condition for reference standards, as well as sample sets for validating nondestructive testing methods. These material conditions include damage, such as the formation of cracks, and damage precursor states, such as the relaxation of residual stresses.

In one embodiment of the invention, a sample having a predetermined material condition is fabricated by positioning a sensor near the material surface, measuring the response of the sensor as the material is processed to change the material condition, and then stopping the processing once the material condition reaches a predetermined level. The sensor remains proximate to the material surface for substantial periods of time to monitor progression of the change in the material condition. The material condition is determined from the sensor response using a predetermined correlation, which can be derived from empirical measurements on other samples or by a model calculation or simulation that accurately predicts the sensor response to the material condition. In one embodiment of the invention, the material condition reflects the presence of a crack and the predetermined level is a size of the crack. In various embodiments of the invention, particularly for relatively conductivity materials, the sensor may be a magnetic field based eddy current sensor or sensor array. In another embodiment of the invention, the sensor may be flexible and conform to the material surface.

The fabrication process for the sample may take a variety of forms, such as mechanical loading, thermal loading, or a combination of the two. In one embodiment of the invention, the processing fatigues the samples so that the material condition is fatigue damage. In one particular embodiment of the invention, the fatigue damage takes the form of a crack. In another embodiment of the invention, the material condition is residual stress. This residual stress can be introduced by the processing or it may relax from a preconditioned level. In one embodiment of the invention, the material is preconditioned prior to process, such as by shot peening the surface to introduce these residual stresses. Alternatively, in another embodiment of the invention, the material is preconditioned by a heat treatment. A related material condition that may be monitored during processing is thermal damage. In yet another embodiment of the invention, the material condition being monitored is the presence and/or size of subsurface flaws.

The shape of the sample material may take a variety of forms. It can be a test coupon, a component, or a full-scale article. In one embodiment of the invention, the shape of the sample material is representative of a complex aircraft component. This component may be coated and the material condition may be a buried or subsurface flaw. In another embodiment of the invention, the sample is a component that is aged in service. In yet another embodiment of the invention, the sample is artificially aged to simulate the material condition resulting from service aging.

In one embodiment of the invention, the sensor response is converted into an effective property measurement and the effective property is then correlated with the material condition. The effective property may be an electrical property of the material, such as an electrical conductivity, magnetic permeability, or dielectric permittivity, or a geometric property, such as a lift-off or a material layer thickness. In another embodiment of the invention, the effective property may be an estimated damage state, such as a dimension or a size of a flaw.

In yet another embodiment of the invention, a matrix of samples is fabricated. This is accomplished by positioning a sensor near the material surface, measuring the response of the sensor as the material is processed to change the material condition, stopping the processing once the material condition reaches a predetermined level, and repeating this process multiple times. In one embodiment of the invention, the same predetermined level for the material condition is used to create multiple samples for nominally similar conditions. This allows a probability density function to be generated, which relates the sensor response to the material condition and allows the uncertainty distribution in the material condition to be assessed. This in turn can be used to assess the capability of the sensor to predict other dependent functions, such as the remaining life for the sample. In another embodiment of the invention, the processing is stopped for a range of predetermined levels. In yet another embodiment of the invention, the material is preconditioned prior to processing, so that the matrix contains a broader range of material variations. In one embodiment of the invention, the material condition may be fatigue damage and in another the preconditioning may be shot peening. In different embodiments of the invention, the matrix of samples may be used as a training set for training the sensor response or as a test set for the evaluation of different sensing methods. In an alternative embodiment of the invention, the matrix design or the distribution of predetermined material condition levels may be based on the statistics used in probability of detection studies.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
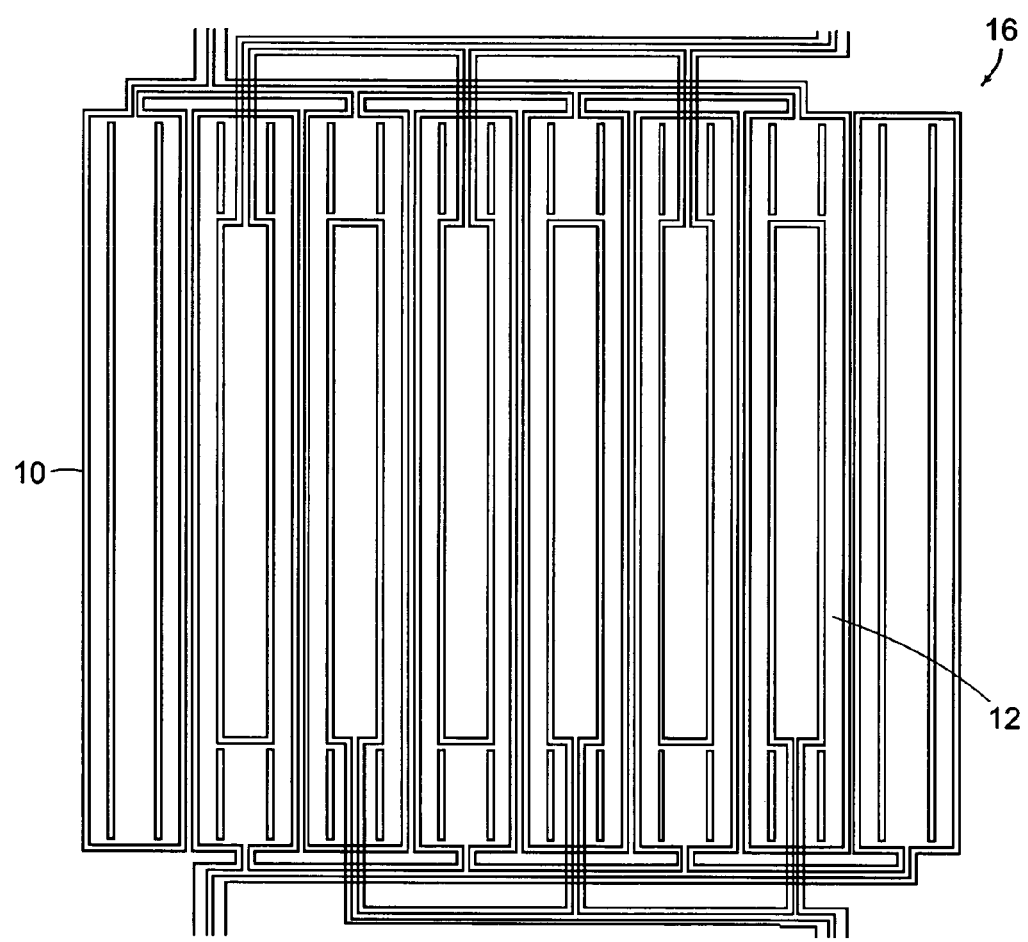
FIG. 1 is an illustration of a spatially periodic field eddy-current sensor.

A description of preferred embodiments of the invention follows.

This application is directed toward the use of sensor and sensor arrays during monitoring of fatigue damage to create reference samples and standards having real fatigue cracks. These standards can be used for sensor standardization in the field and reliability studies for validating sensors or measurement methods. One objective may be to generate specimens with realistic cracks under conditions as close to reality as feasible, and even to generate conditions of interest in actual components, if necessary. Conditions of interest may include cracks in holes, on curved surfaces, on shot peened surfaces, in and under coatings and at buried surfaces. One embodiment of the invention uses permanently mounted sensors, such as MWM®-Array eddy current sensors, to detect crack initiation and monitor crack growth. These sensors have been used in fatigue tests of coupons and components as well as full-scale fatigue test articles. Using them may help account for the effects of mechanical or thermal overloading events and for generating conditions of interest in composites, coatings, shot peened specimens and even specimens with specified high-temperature damage, e.g., creep damage. One embodiment of the invention uses networks of permanently mounted MWM-Array eddy current sensors (either on the surface or between layers) to monitor initiation and growth of cracks. Examples of specimens may include aluminum alloy and steel fatigue specimens, engine component materials and complex constructs, such as lap joints with multiple site damage initiating below the surface.

An important aspect of one embodiment of this invention is that the sensor geometry and the interaction of the interrogating fields from the sensor with the test material are modeled accurately. One such sensor geometry is the conformable eddy-current sensor of the Meandering Winding Magnetometer (MWM®), described in U.S. Pat. Nos. 5,015,951, 5,453,689, and 5,793,206, incorporated by reference herein in their entirety. The MWM is a "planar," conformable eddy-current sensor that is designed to support quantitative and autonomous data interpretation methods. These methods, called grid measurement methods, permit crack detection on curved surfaces without the use of crack standards and provide quantitative images of absolute electrical properties (conductivity and permeability) and coating thickness without requiring field reference standards (i.e., calibration is performed in "air," away from conducting surfaces). MWM sensors and MWM-Arrays can be used for a number of applications, including fatigue monitoring and inspection of structural components for detection of flaws, degradation and microstructural variations as well as for characterization of coatings and process-induced surface layers. Characteristics of these sensors and sensor arrays include directional multi-frequency magnetic permeability or electrical conductivity measurements over a wide range of frequencies, e.g., from 250 Hz to 40 MHz with the same MWM sensor or MWM-Array, high-resolution imaging of measured permeability or conductivity, rapid permeability or conductivity measurements with or without a contact with the surface, and a measurement capability on complex surfaces with a hand-held probe or with an automated scanner.

FIG. 1 illustrates the basic geometry of an MWM sensor 16, a detailed description of which is given in U.S. Pat. Nos. 5,453,689, 5,793,206, and 6,188,218 and U.S. patent application Ser. Nos. 09/666,879 and 09/666,524, both filed on Sep. 20, 2000, the entire teachings of which patents and applications are incorporated herein by reference in their entirety. The sensor includes a primary winding 10 having extended portions for creating the magnetic field and secondary windings 12 within the primary winding for sensing the response. The primary winding is fabricated in a spatially periodic pattern with the dimension of the spatial periodicity termed the spatial wavelength $\lambda$. A current is applied to the primary winding to create a magnetic field and the response of the material under test (MUT) to the magnetic field is determined through the voltage measured at the terminals of the secondary windings. This geometry creates a magnetic field distribution similar to that of a single meandering primary winding. A single element sensor has all of the sensing elements connected together. The net magnetic vector potential produced by the current in the primary can be accurately modeled as a Fourier series summation of spatial sinusoids, with the dominant mode having the spatial wavelength $\lambda$. For an MWM-Array, the responses from individual or combinations of the secondary windings can be used to provide a plurality of sense signals for a single primary winding construct as described in U.S. Pat. No. 5,793,206 and Re. 36,986.

Figure 2:
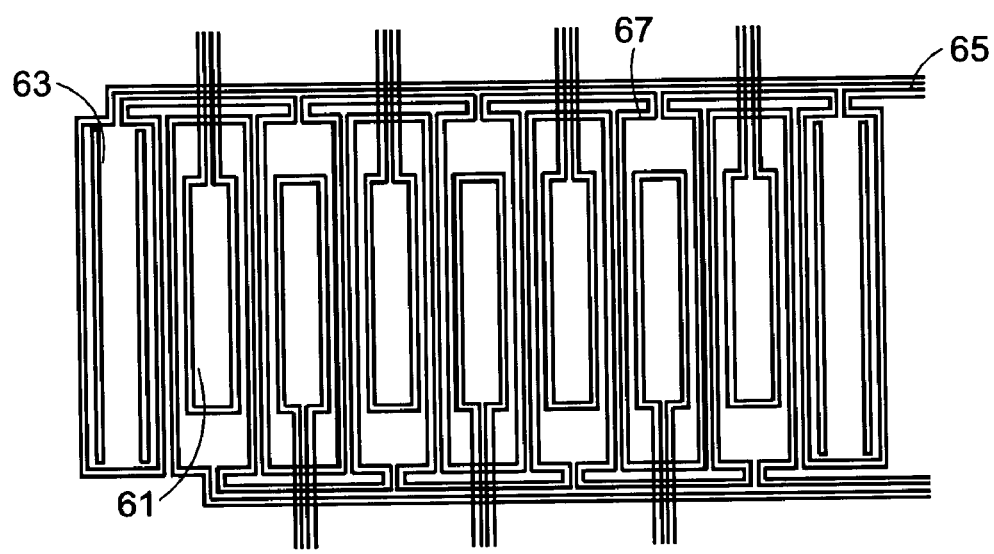
FIG. 2 is a plan view of sensor array with a single primary winding and an array of sensing elements with connections to each individual element.

The MWM-Arrays typically have one or more drive windings, possibly a single rectangle, and multiple sensing elements for inspecting the test material. Some of the motivation for the use of multiple sensing elements is to increase the spatial resolution of the material being characterized without loss of coverage, to add additional information for use in the estimation of multiple unknown material properties, and to cover large inspection areas in a faster time. Example scanning sensor arrays are described in detail in U.S. patent application Ser. No. 10/102,620, filed Mar. 19, 2002, and Ser. No. 10/010,062, filed Mar. 13, 2001, the entire teachings of which are incorporated herein by reference. FIG. 2 shows a schematic view of a permanently mounted seven-element array. Connections are made to each of the individual secondary elements 61. Dummy elements 63 are placed on the outside meanders of the primary 65. As described in U.S. Pat. No. 6,188,218, the secondaries are set back from the primary winding connectors 67 and the gap between the leads to the secondary elements are minimized. This flexible array can be inserted into a hole within the gage section of a fatigue specimen to monitor crack initiation and initial crack propagation or placed flush against a surface to monitor crack propagation.

Figure 3:
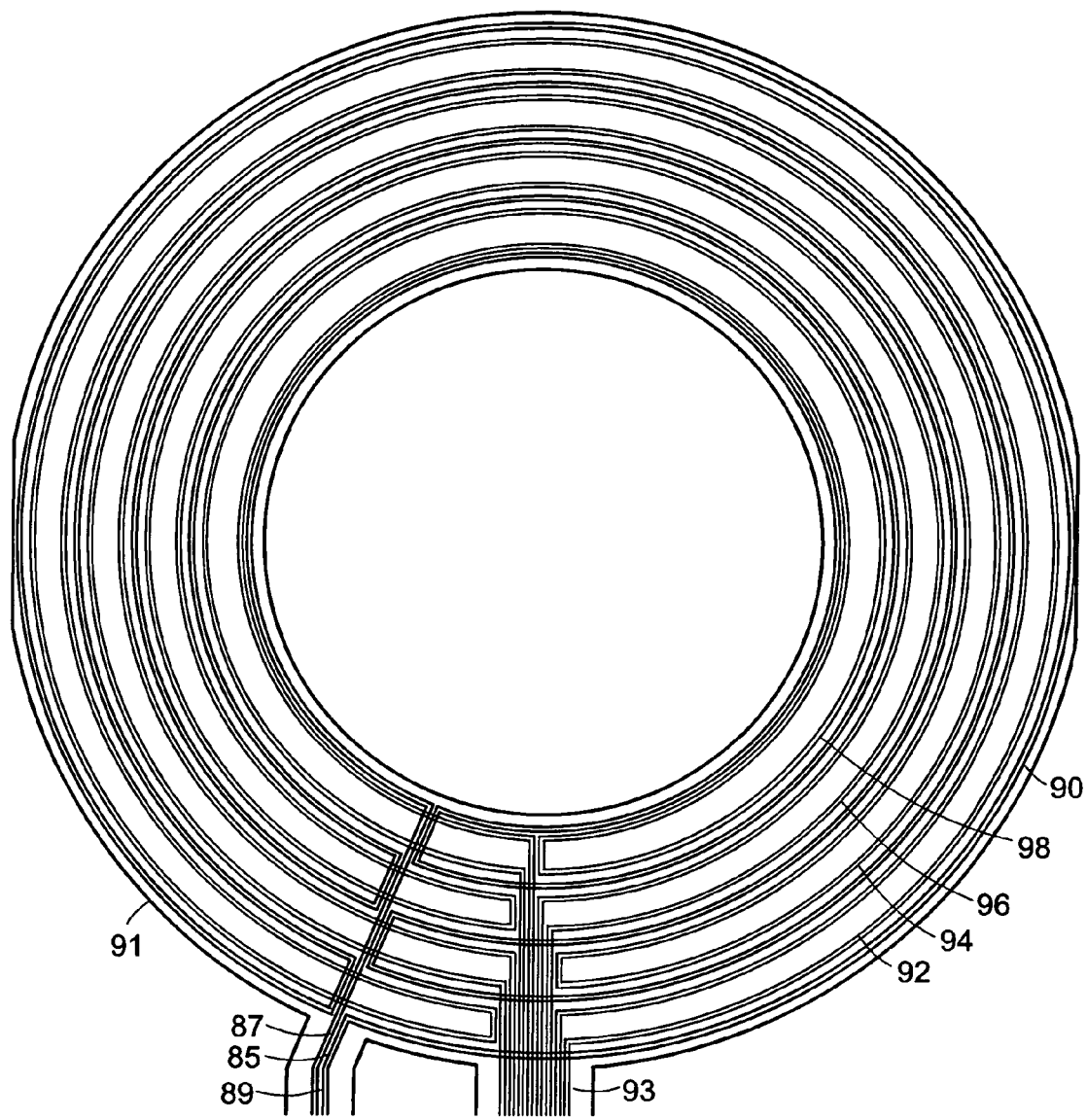
FIG. 3 is a plan view of a circular sensor array for crack detection and crack length measurement.

FIG. 3 illustrates a circularly symmetric embodiment of an MWM-Array. This MWM-Rosette maintains the spatial periodicity of the magnetic field in the radial direction with primary winding 90. Secondary elements 92, 94, 96, and 98 provide complete coverage around the circumference of the sensor and can be used to detect cracks and determine the crack length. The gap 89 between the primary winding conductors 85 and 87 is minimized to reduce any stray magnetic fields that may affect the measurements. The first active sensing (secondary) element is located as close as possible to the inside of the sensor to enable early detection of cracks. The primary winding 90 is fabricated onto one side of a substrate 91 while the secondary elements 92, 94, 96, and 98 are fabricated onto the opposite side of the substrate. Individual connections 93 are made to each of the secondary elements for independent measurements of the response of each element. Alternatively, the net signal from all of the elements can be obtained by connecting the loops together. As another alternative, other shapes can be employed where the conducting segments follow a contour of the test material geometry, such as a curved edge.

The circular rosette configuration is useful for crack detection and location around circularly symmetric regions, such as around fasteners. The rosette configuration can also be used in areas where the stress distribution and the crack initiation point and growth direction may not be known because of complex component geometry or service related repairs.

The MWM sensor and sensor array structure can be produced using micro-fabrication techniques typically employed in integrated circuit and flexible circuit manufacture. This results in highly reliable and highly repeatable (i.e., essentially identical) sensors, which have inherent advantages over the coils used in conventional eddy-current sensors. The lack of reproducibility with conventional coils introduces severe requirements for calibration of the sensors (e.g., matched sensor/calibration block sets). In contrast, duplicate MWM sensor tips have nearly identical magnetic field distributions around the windings because standard micro-fabrication (etching) techniques have both high spatial reproducibility and resolution. Because the sensor is also designed to produce a spatially periodic magnetic field in the MUT, the sensor response may be accurately modeled, which dramatically reduces calibration requirements. For example, calibration in air may be used to measure an absolute electrical conductivity without calibration standards, which makes the sensor geometry well-suited to surface mounted or embedded applications where calibration requirements will be necessarily relaxed.

Multiplexing between the elements can be performed for measuring the response of the individual sensing elements in an array. However, this may significantly reduce the data acquisition rate, so a more preferable approach is to use an impedance measurement architecture that effectively allows the acquisition of data from all of the sense elements in parallel. Furthermore, the ability to measure the MUT properties at multiple frequencies may extend the capability of the inspection to better characterize the material and/or geometric properties under investigation. This type of instrument is described in detail in U.S. patent application Ser. No. 10/155,887, filed May 23, 2002, the entire teachings of which are incorporated herein by reference. The use of multiple sensing elements with one meandering drive and parallel architecture measurement instrumentation then permits high image resolution in real-time and sensitivity with relatively deep penetration of fields into MUT.

One efficient method for converting the response of the MWM sensor into material or geometric properties is to use grid measurement methods. These methods map two known values, such as the magnitude and phase or real and imaginary parts of the sensor impedance, into the properties to be determined and provide for a real-time measurement capability. The measurement grids are two-dimensional databases that can be visualized as "grids" that relate two measured parameters to two unknowns, such as the magnetic permeability (or electrical conductivity) and lift-off (where lift-off is defined as the proximity of the MUT to the plane of the MWM windings). For the characterization of coatings or surface layer properties, three- (or more)-dimensional versions of the measurement grids called lattices and hypercubes, respectively, can be used. Alternatively, the surface layer parameters can be determined from numerical algorithms that minimize the least-squares error between the measurements and the predicted responses from the sensor, or by intelligent interpolation search methods within the grids, lattices or hypercubes.

An advantage of the measurement grid method is that it allows for real-time measurements of the absolute electrical properties of the material and geometric parameters of interest. The database of the sensor responses can be generated prior to the data acquisition on the part itself, so that only table lookup and interpolation operations, which are relatively fast, need to be performed after measurement data is acquired. Furthermore, grids may be generated for the individual elements in an array so that each individual element can be lift-off compensated to provide absolute property measurements, such as the electrical conductivity. This compensation reduces the need for extensive calibration standards. In contrast, conventional eddy-current methods that use empirical correlation tables that relate the amplitude and phase of a lift-off compensated signal to parameters or properties of interest, such as crack size or hardness, require extensive calibrations using standards and instrument preparation.

Figure 4:
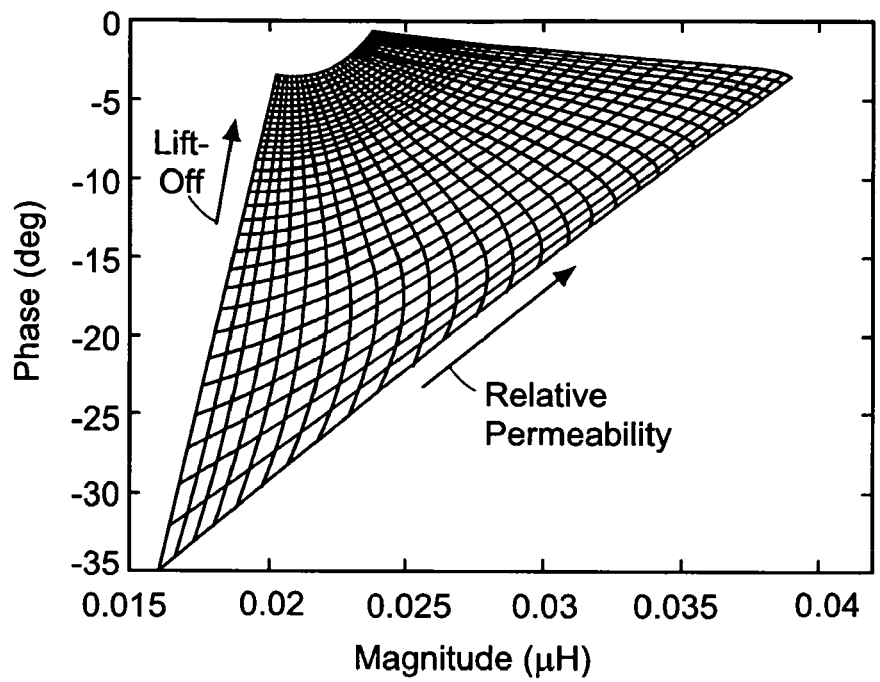
FIG. 4 illustrates a representative measurement grid relating the magnitude and phase of the sensor terminal impedance to the lift-off and magnetic permeability.
Figure 5:
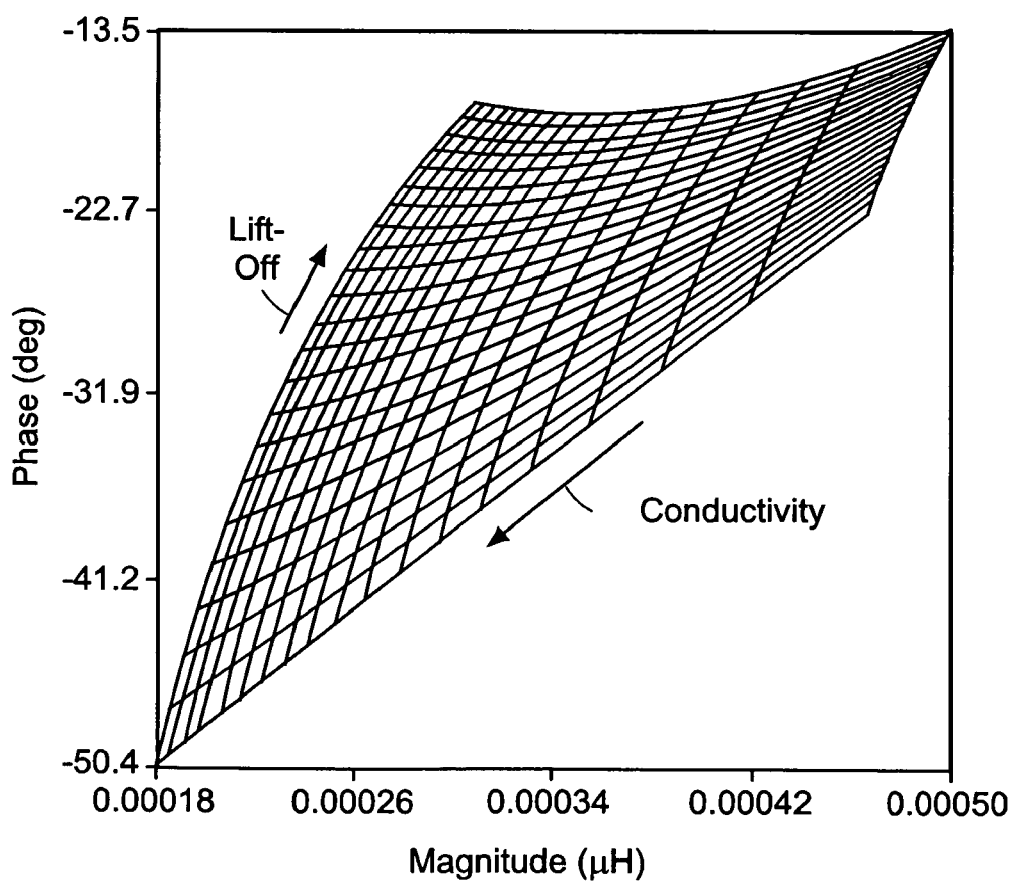
FIG. 5 illustrates a representative measurement grid relating the magnitude and phase of the sensor terminal impedance to the lift-off and electrical conductivity.

For ferromagnetic materials, such as most steels, a measurement grid can provide a conversion of raw data to magnetic permeability and lift-off. A representative measurement grid for ferromagnetic materials is illustrated in FIG. 4. A representative measurement grid for a low-conductivity nonmagnetic alloy (e.g., titanium alloys, some superalloys, and austenitic stainless steels) is illustrated in FIG. 5. For coated materials, such as cadmium and cadmium alloys on steels, the properties of the coatings can be incorporated into the model response for the sensor so that the measurement grid accurately reflects, for example, the permeability variations of substrate material with stress and the lift-off. Lattices and hypercubes can be used to include variations in coating properties (thickness, conductivity, permeability), over the imaging region of interest. The variation in the coating can be corrected at each point in the image to improve the measurement of permeability in the substrate for the purpose of imaging stresses. The effective property can also be a layer thickness, which is particularly suitable for coated systems. The effective property could also be some other estimated damage state, such as the dimension of a flaw or some indication of thermal damage for the material condition.

Figure 7:
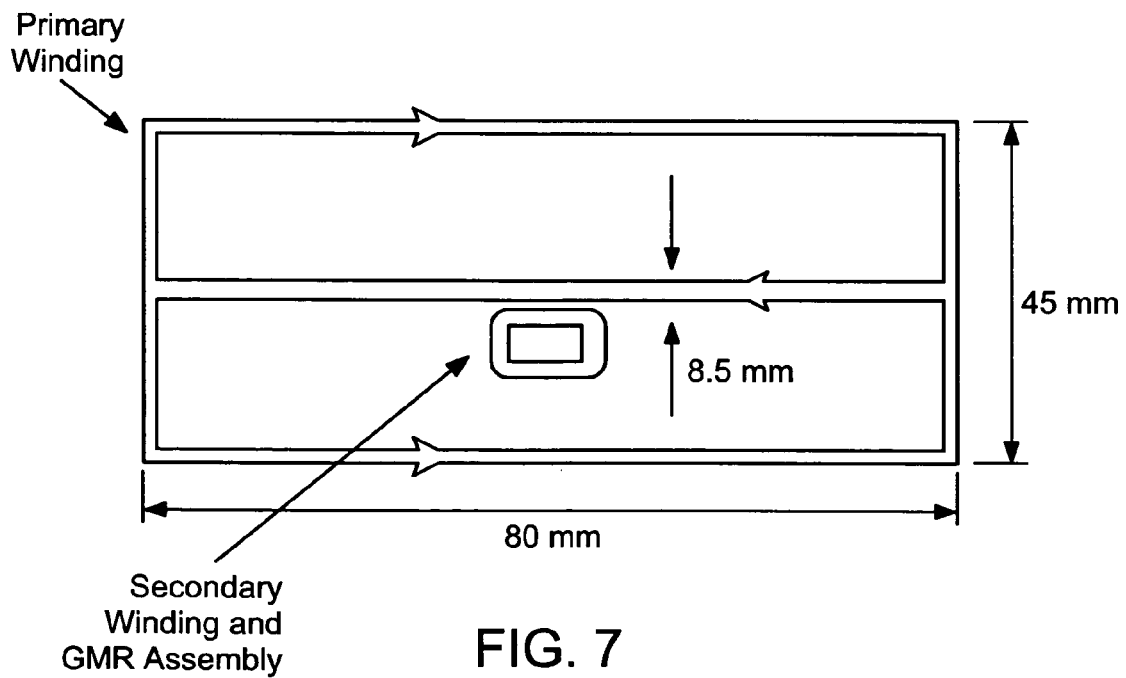
FIG. 7 illustrates a layout for a single turn Cartesian geometry GMR magnetomer.

In addition to inductive coils, other types of sensing elements, such as Hall effect sensors, magnetoresistive sensors, SQUIDS, and giant magnetoresistive (GMR) devices, can also be used for the measurements. The use of GMR sensors for characterization of materials is described in more detail in U.S. patent application Ser. No. 10/045,650, filed Nov. 8, 2001, the entire teachings of which are incorporated herein by reference. An example rectangular or Cartesian-geometry GMR-based magnetometer is illustrated in FIG. 7. Conventional eddy-current sensors are effective at examining near surface properties of materials but have a limited capability to examine deep material property variations. GMR sensors respond to magnetic fields directly, rather than through an induced response on sensing coils, which permits operation at low frequencies, even DC, and deeper penetration of the magnetic fields into the test material. The GMR sensors can be used in place of sensing coils, conventional eddy-current drive coils, or sensor arrays. Thus, the GMR-based sensors can be considered an extension of conventional eddy-current technology that provides a greater depth of sensitivity to hidden features and are not deleteriously affected by the presence of hidden air gaps or delaminations.

For insulating or weakly conducting materials, such as fiberglass composites, capacitive or dielectric sensors may be used. The sensors are the electromagnetic dual to the inductive sensors, with electric fields taking the place of magnetic fields for inspecting the materials and can be used to monitor stress or temperature, moisture content or contamination or overload of fatigue in adhesives, epoxies, glass, oil, plastics and in single or multiple layered media. Here the conductivity and dielectric constant or complex permittivity and layer thicknesses are measured using the same methods as for magnetic field sensing. In one such electric field method embodiment of the invention, multiple layers of material are added to a base material with each layer sensitive to different chemicals or biological materials.

Figure 6:
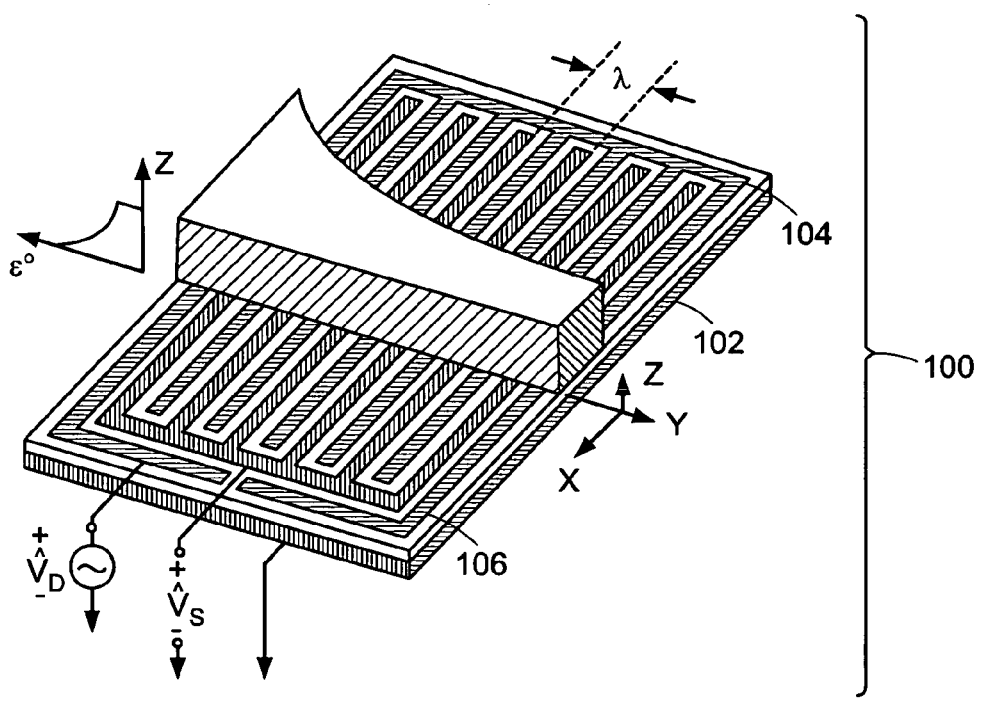
FIG. 6 illustrates a representative single wavelength interdigitated electrode dielectrometer with spatially periodic driven and sensing electrodes of wavelength λ that can measure dielectric properties of the adjacent material for remotely monitoring the temperature of a plate.

A representative single sided sensor geometry is shown in FIG. 6. The application of a sinusoidally time varying potential of angular frequency $\omega=2\pi f$ results in the flow of a terminal current, whose magnitude and phase is dependent on the complex permittivity of the material. The capacitive sensor 100 has interdigitated electrodes as presented in U.S. Pat. Nos. 4,814,690, 6,380,747, and 6,486,673 and in U.S. patent application Ser. No. 10/040,797, filed Jan. 7, 2002, and Ser. No. 10/225,406, filed Aug. 20, 2002, the entire teachings of which are hereby incorporated by reference. This sensor 102 utilizes a pair of interdigitated electrodes 104 and 106 to produce a spatially periodic electric field. The electrodes are adjacent to the material of interest with an insulating substrate and a ground plane on the other side of the substrate. One of the two electrodes, 104, is driven with a sinusoidally varying voltage $v_D$ while the other, 106, is connected to a high-impedance buffer used to measure the magnitude and phase of the floating potential $v_S$ or to a virtually grounded amplifier to measure the magnitude and phase of the terminal current I. The periodicity of the electrode structure is denoted by the spatial wavelength $\lambda=2\pi/k$, where k is the wavenumber.

The following examples illustrate how these methods can be used to generate specimens with real cracks that represent the actual cracks seen in service or similar to cracks formed as a result of manufacturing deficiencies. There is a critical need for such specimens because crack detection requirements are becoming more severe. Crack morphology variations are a major source of NDI response variation, not only for eddy current sensing but also for other methods such as penetrant testing and ultrasonic testing. Thus, specimens with cracks grown without starter notches not only in machined, but also in shot peened or coated materials, can provide real value in assessing true NDI performance under probability of detection (POD) and other performance studies. Existing methods to grow cracks from EDM notches and then remove the notches are impractical for shot peened parts, since the shot peened surface would be removed. Also, for growing cracks under coatings and on complex components, cracks created without starter notches are essential to test real NDI performance. Moreover, small and shallow fatigue cracks initiated without starter notches tend to form in clusters and are not necessarily aligned. Thus, they are representative of small cracks observed in real structures. Small cracks in such clusters can be missed by differential eddy current sensors and also by a number of other conventional NDI methods.

Figure 8:
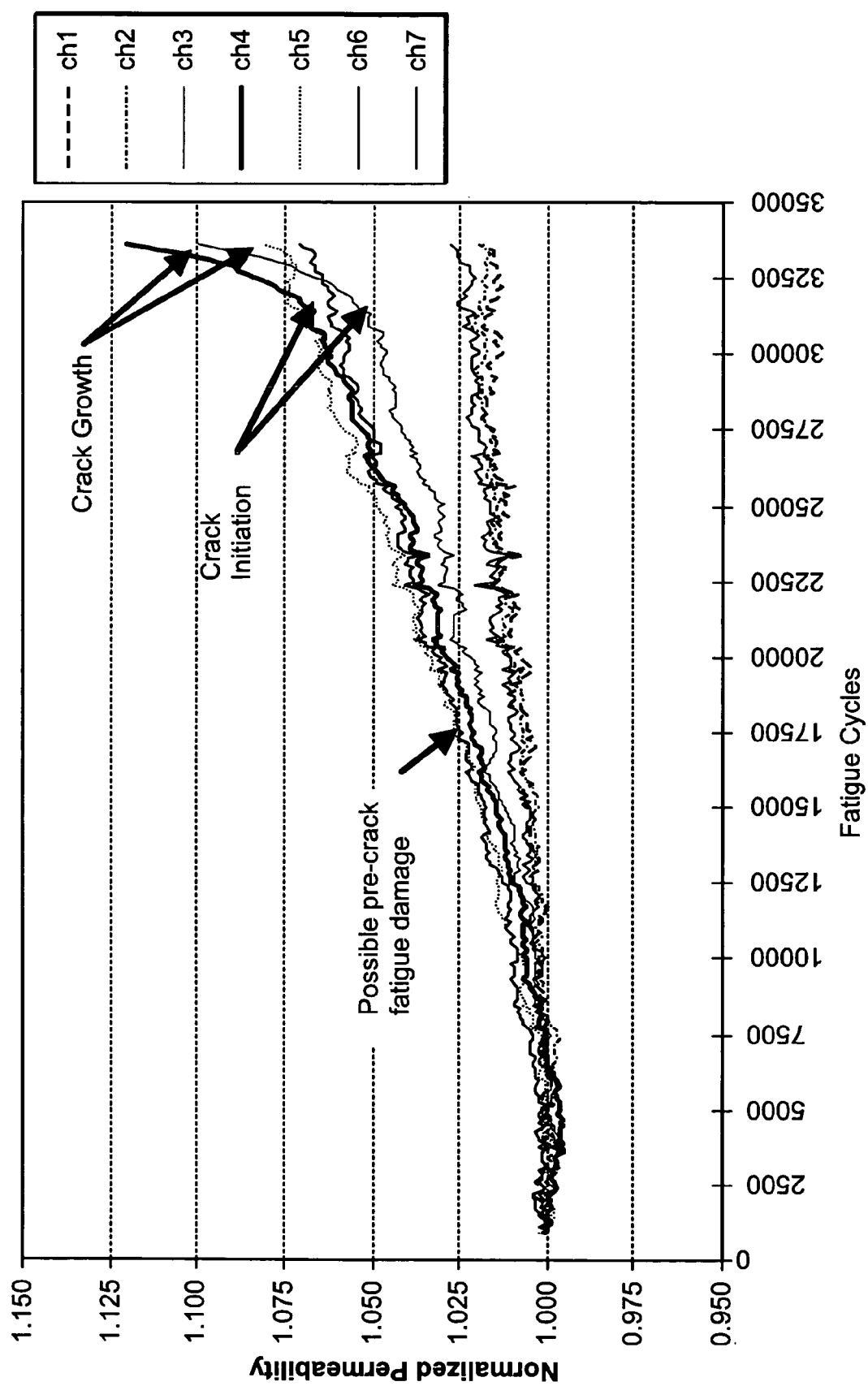
FIG. 8 illustrates a plot of normalized permeability against the number of fatigue cycles for a shot peened 4340 steel specimen.

FIG. 8 illustrates the permeability changes during a fatigue test of a shot peened 4340 low alloy steel specimen, representative of landing gear, monitored with a 7-channel MWM-Array. There is virtually no change in the measured permeability up to 7,000 cycles. The change in the permeability slope in the four centrally located channels at about 7,000 cycles is most likely associated with residual stress relaxation and precrack fatigue damage. This fatigue damage stage extends, perhaps, up to 17,000 cycles followed by initiation and extension of multiple microcracks. Two of the channels show a significant permeability increase at 32,000 cycles indicating coalescence of closely spaced cracks and faster crack growth. In this case the test was stopped when the normalized permeability indicated accelerated crack growth at two locations. The test could also have been stopped earlier at a different predetermined level, such as a normalized permeability of 1.025 or 1.050, if the precrack stage was of interest. After the test, the area was scanned with a scanning MWM-Array. An image of the magnetic permeability produced with the MWM-Array revealed a fatigue damage zone with cracks at the two locations identified first by the permanently mounted MWM-Array during the fatigue test. These cracks were not detected using conventional eddy current test (ET), ultrasonic test (UT) or fluorescent penetrant testing performed by Level III inspectors at an aerospace original equipment manufacturer (OEM). An examination in a scanning electron microscope (SEM) confirmed the presence of the cracks at these two locations, but the longest crack detected in the SEM was only 200 μm (0.008 in.) long at the surface. Subsequently performed fractography detected two cracks that are significantly longer than the cracks revealed by SEM. The MWM-Array detections are generally consistent with the fractography findings.

Figure 9:
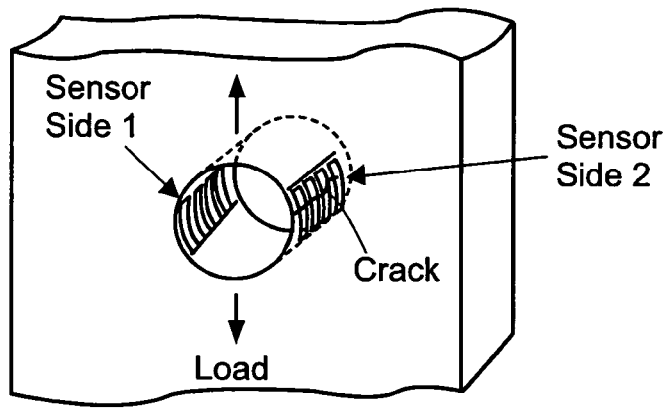
FIG. 9 illustrates an illustration of two MWM-Arrays mounted inside a fatigue test coupon.

FIG. 9. illustrates an example application of two MWM-Arrays of FIG. 2 mounted inside a hole of a test coupon that is subsequently cyclically loaded. The MWM-Arrays mounted within the hole can be used to detect shallow part-through wall cracks (e.g., tunneling cracks that have initiated inside the hole but have not propagated to the outside surface). The MWM-Arrays can also be placed around the circumference of a cylindrical or hyperbolical gage section. Multi-frequency MWM measurements can provide diagnostic information to monitor crack propagation in both length and depth directions. In alternative embodiments of the invention, the arrays may be mounted on the adjacent side surfaces of the fatigue test coupon as well. MWM-Arrays on the sides are used once a "corner" or through-wall crack (i.e., one that has reached either or both outer surfaces) forms. The crack length can be inferred from the MWM measured effective conductivity since the MWM measured conductivity change correlates with crack length even for relatively short surface cracks and for cracks deeper than the MWM penetration depth. The correlation with length is expected to be even more robust for through-wall cracks, so that a single sensing element MWM may be used for regions outside the hole as well. This type of application is suitable for monitoring crack propagation with fatigue cycles (da/dN) during complex component testing. These complex components can be aircraft components, such as landing gear, that may also be coated. The flaws may even be subsurface or buried beneath coatings or other material layers.

Figure 10:
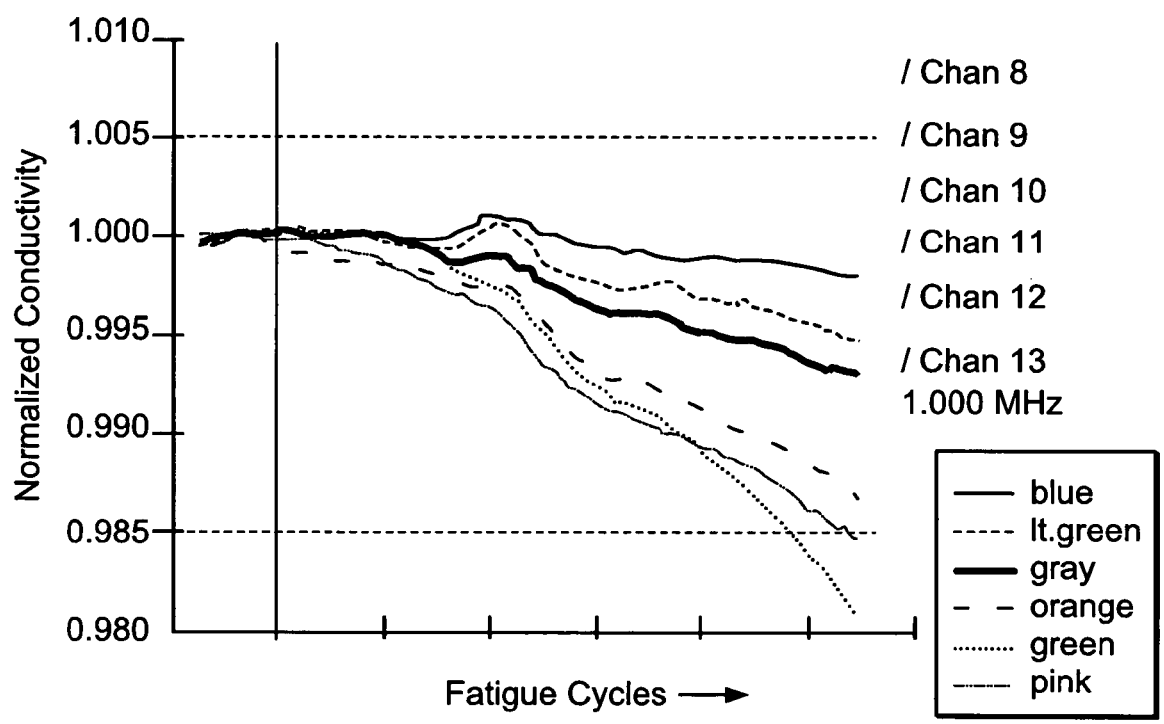
FIG. 10 illustrates example normalized conductivity data for an MWM-Array mounted to the right side of a hole in an aluminum alloy fatigue test coupon.
Figure 11:
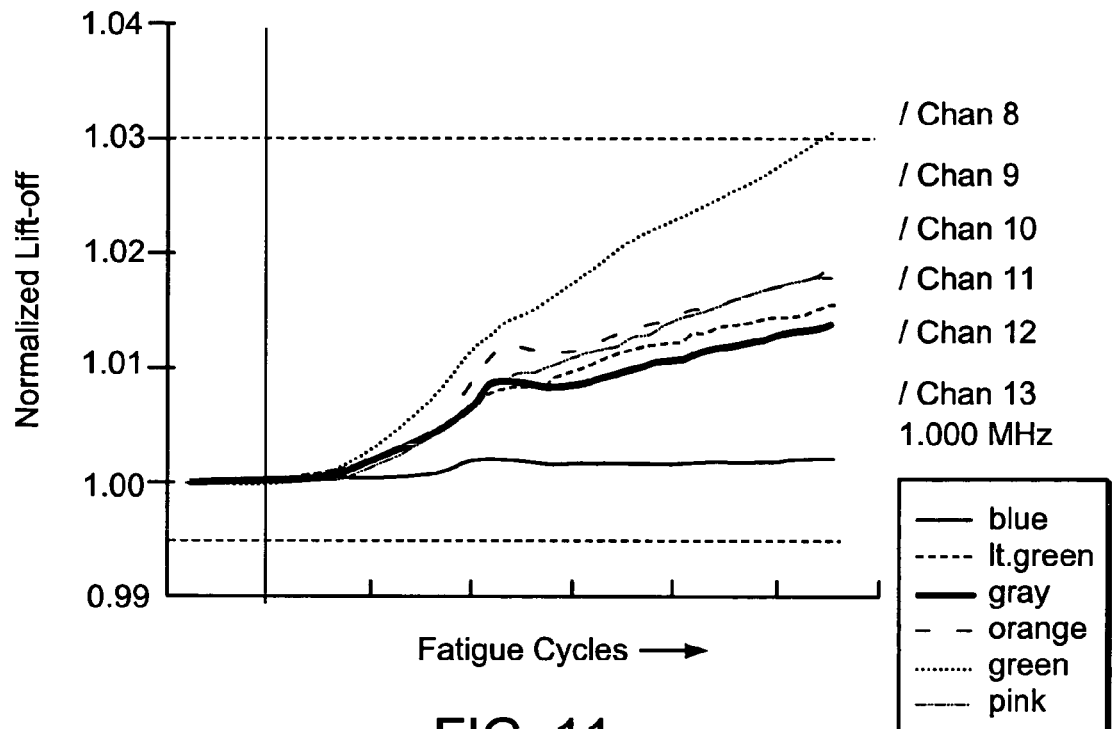
FIG. 11 illustrates example normalized lift-off data for an MWM-Array mounted to the right side of a hole in an aluminum alloy fatigue test coupon.
Figure 12:
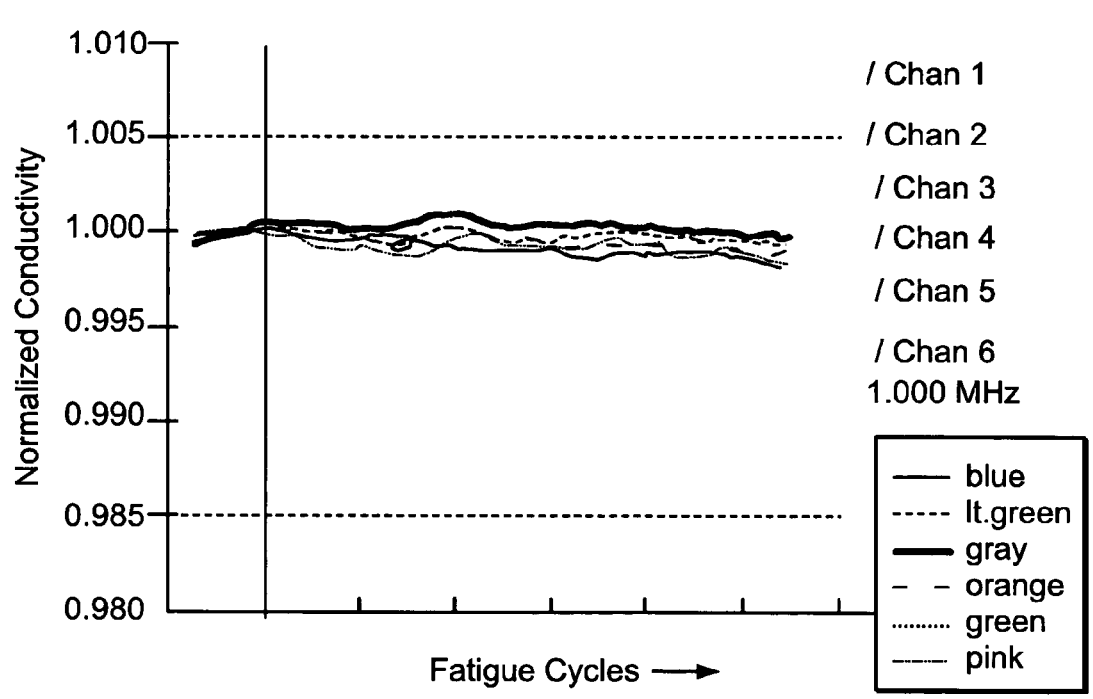
FIG. 12 illustrates example normalized conductivity data for an MWM-Array mounted to the left side of a hole in an aluminum alloy fatigue test coupon.
Figure 13:
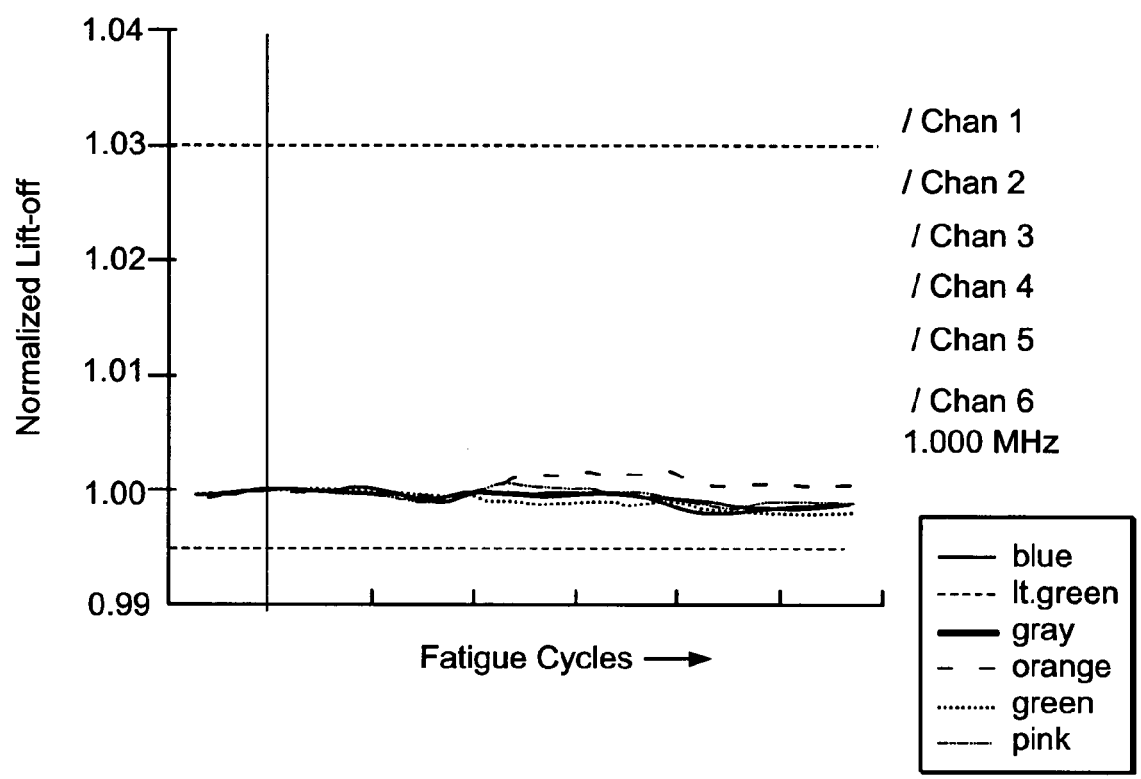
FIG. 13 illustrates example normalized lift-off data for an MWM-Array mounted to the left side of a hole in an aluminum alloy fatigue test coupon.

Surface mounted MWM-Arrays have demonstrated an on-line capability to monitor cumulative fatigue damage during load cycling. FIGS. 10–13 illustrate some representative results for the configuration of FIG. 9 for an aluminum alloy specimen, where the measurement data has been converted into an effective conductivity and lift-off for each element of the sensor array. The data for the array on the right side of the hole is shown in FIGS. 10 and 11, while the data for the array on the left side of the hole is shown in FIGS. 12 and 13. In each case, the effective property data is normalized by dividing each value by the average of the low fatigue cycle data. In other cases, the intermediate cycle number data may be more appropriate for the normalization. As the number of fatigue cycles increases, the effective conductivity decreases and the effective lift-off increases for some of the elements of the array on the right side of the hole, indicating crack growth. The lift-off data also provides a measure of surface roughening related to precrack fatigue damage. For the array on the lefts side of the hole, the effective properties remain essentially constant.

Figure 14:
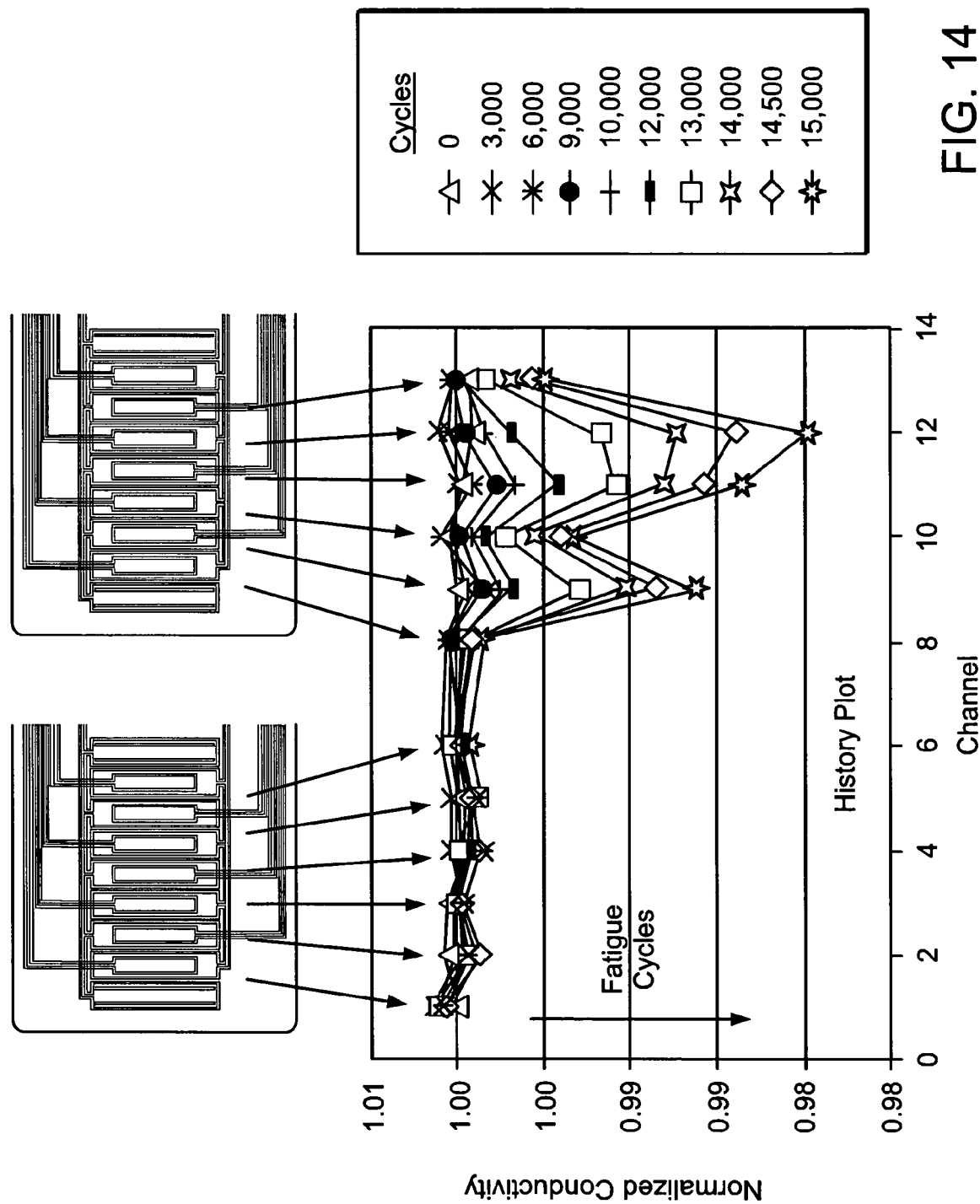
FIG. 14 illustrates a history plot of the normalized conductivity data for MWM-Arrays mounted inside a hole in an aluminum alloy fatigue test coupon.

FIG. 14 illustrates a history plot of the data, where the response of each of the sense elements positioned along the hole is plotted for several different numbers of fatigue cycles. The response from the sensor array on the right indicates that two cracks were being monitored. Using this approach, tests have been stopped with cracks as small as 40 um (0.0016 in.). Using other specimens run to failure, the entire response throughout the fatigue life, i.e., from crack initiation to failure, can be obtained. This then provides a reference for the effective property variation with fatigue life so that other tests can be stopped at various stages of crack initiation and propagation. This also provides samples and standards having real cracks, with real crack morphologies. In this case, the processing performed on the sample was fatigue by mechanical loading. Other types of processing include thermal loading and the combination of mechanical and thermal loading. Of course, this approach can also be used for other types of specimen geometries. In each of the these situations, the sensor remains proximate to the material surface for substantial periods of time, and in some cases the entire duration of the testing, to monitor progression of the material condition.

Figure 15:
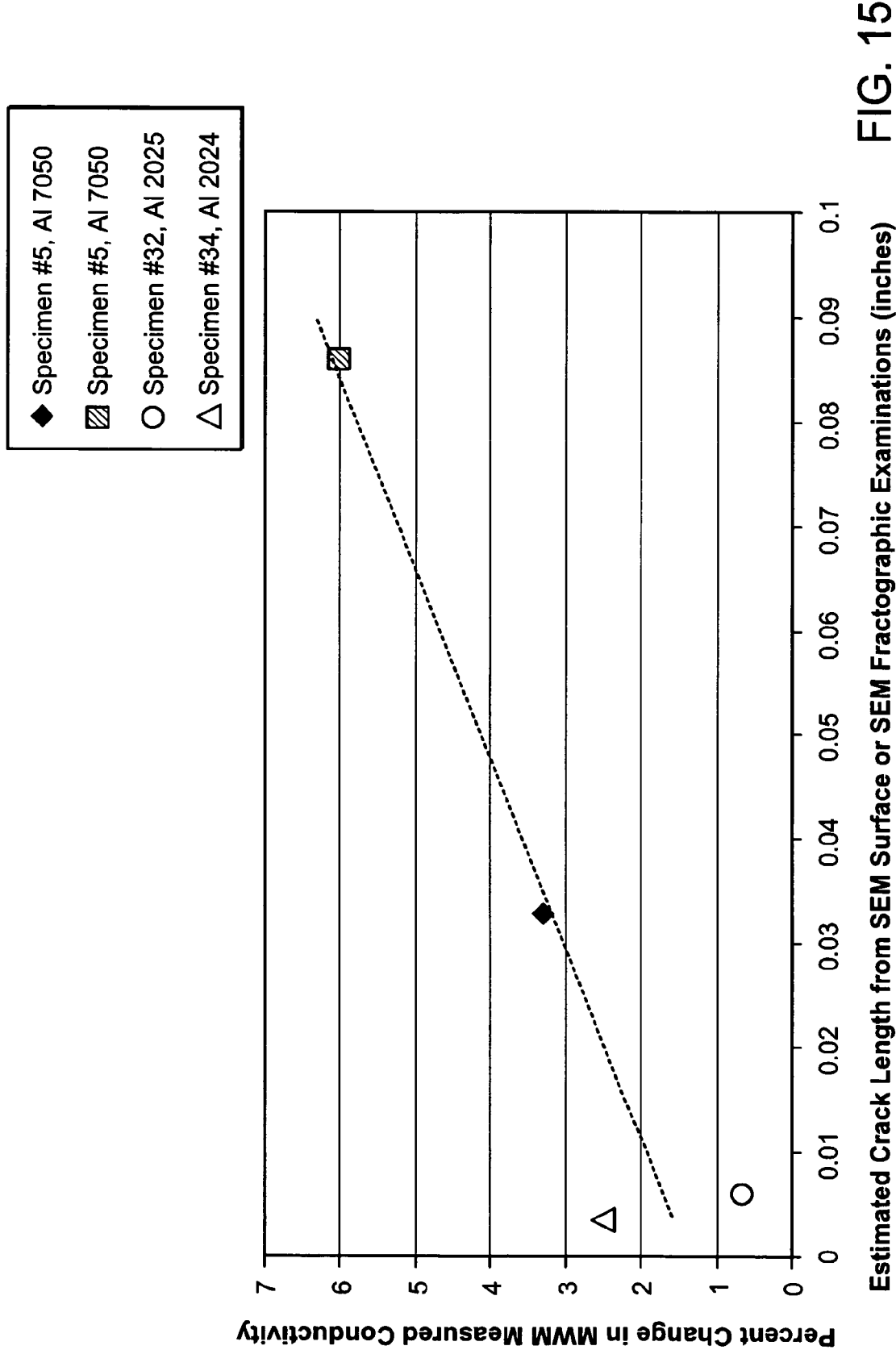
FIG. 15 illustrates the correlation between the MWM measured conductivity changes and crack length estimated from SEM.

A representative correlation between crack size and effective property response is illustrated in FIG. 15. This type of empirical correlation can be used to set the predetermined material condition level for stopping the test. Similarly, model calculations can be used to generate the correlation, such as relate the sensor response or signal to the size of a crack.

Figure 16:
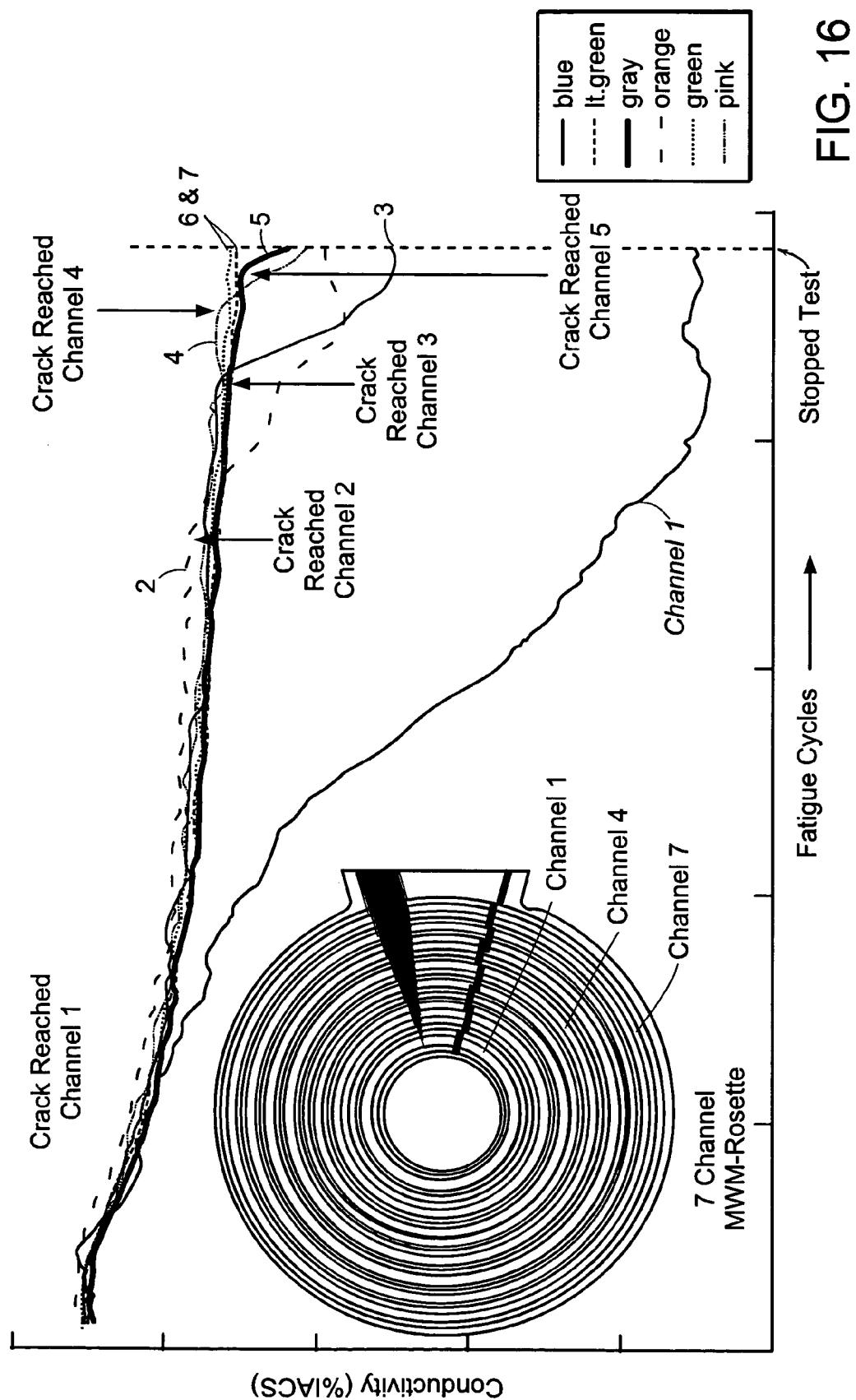
FIG. 16 illustrates an effective conductivity response for an MWM-Rosette mounted between aluminum alloy layers and around a fastener of a fatigue test specimen.

FIG. 16 illustrates another example and provides data from a fatigue test with an MWM-Rosette mounted around a hole in an aluminum dogbone specimen. Each channel number corresponds to an individual annular sensing element, with channel 1 being closest to the fastener and channel 7 the farthest from the fastener. The conductivity drop in each channel occurs when the crack approaches the primary winding on the inner side of the sense. Knowledge of the sensor geometry and the number of cycles when each channel shows a reduction in conductivity then allows crack growth curves to be generated. Similar results may be obtained when this type of sensor is mounted around a fastener and under the head or nut or even between layers.

Figure 17:
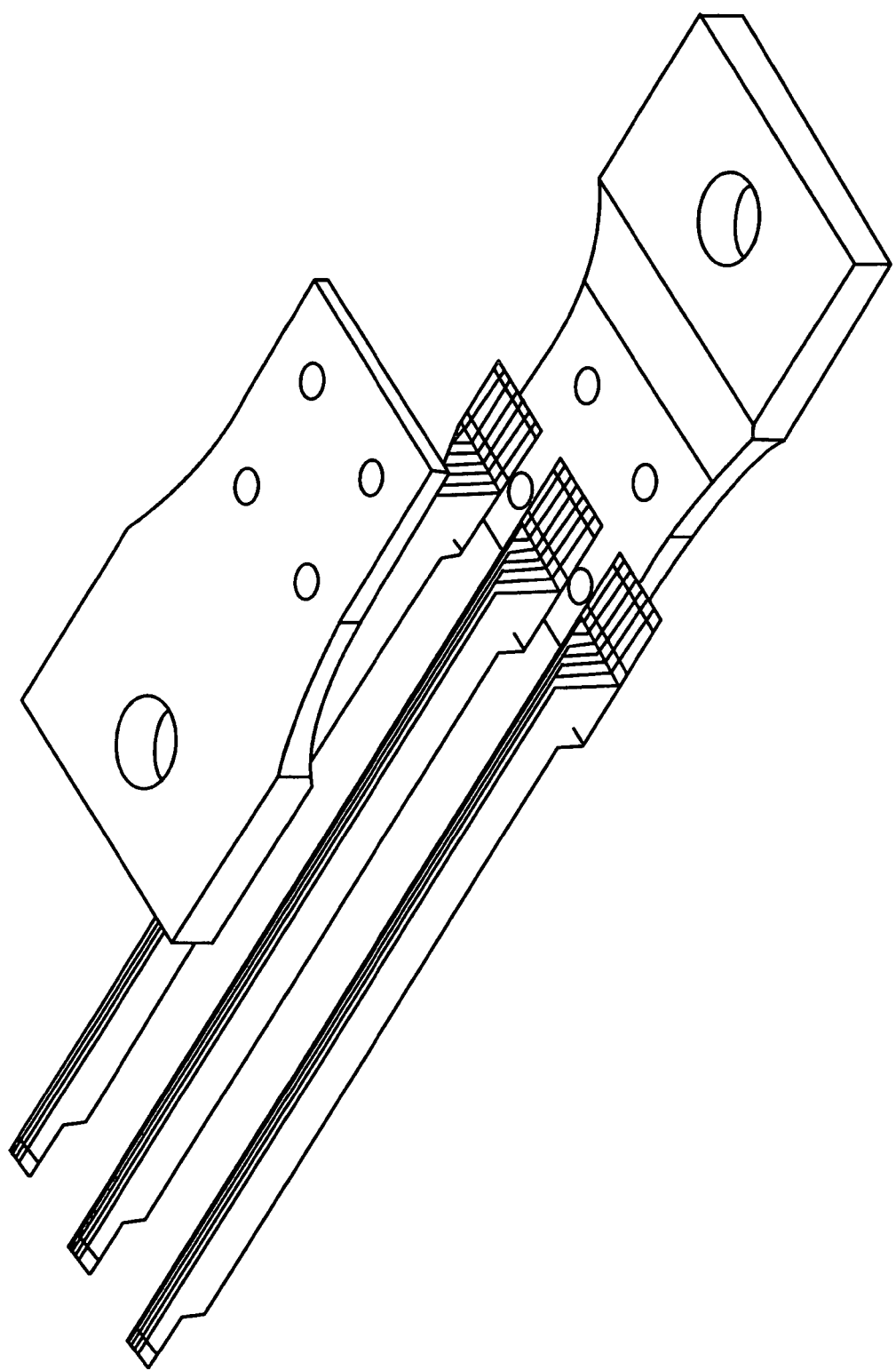
FIG. 17 is a schematic of several linear arrays mounted along a test row in a four-hole test specimen.

FIG. 17 illustrates yet another example where linear arrays are mounted along a test row in a four hole fatigue test specimen. A linear array is placed on the ligament between two of the holes while two additional arrays are placed on the outside ligaments with only a fraction of the sense elements over the test material. The sensor arrays are typically mounted to the reaction plate, on which the cracks are not expected to grow. The sensor arrays then monitor crack growth in the ligaments of the row of fasteners in a test plate. Crack growth in the non-test row of fastener holes can be achieved by cold-working the holes and by adding stiffener plates to reduce spurious bending moments.

Figure 18:
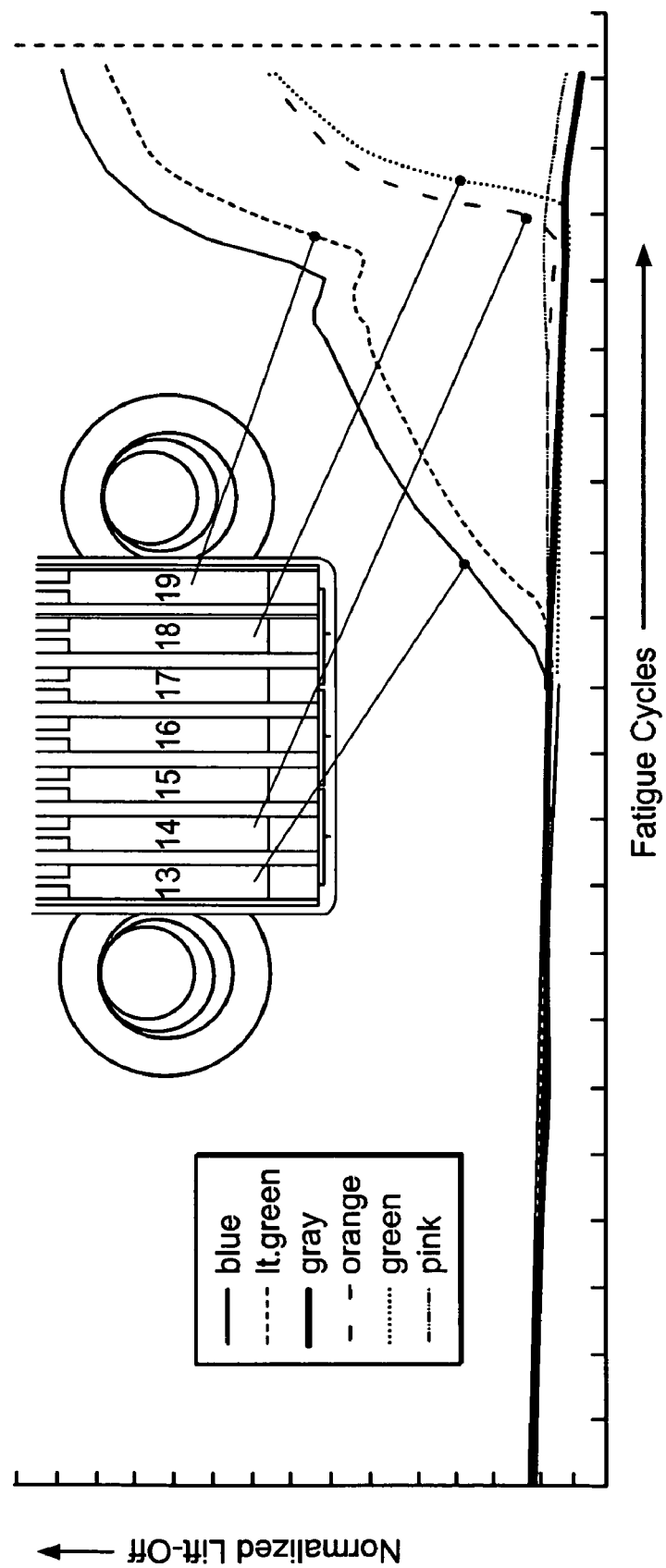
FIG. 18 illustrates the effective lift-off variation for a linear sensor array mounted between a pair of holes in a fatigue test specimen.
Figure 19:
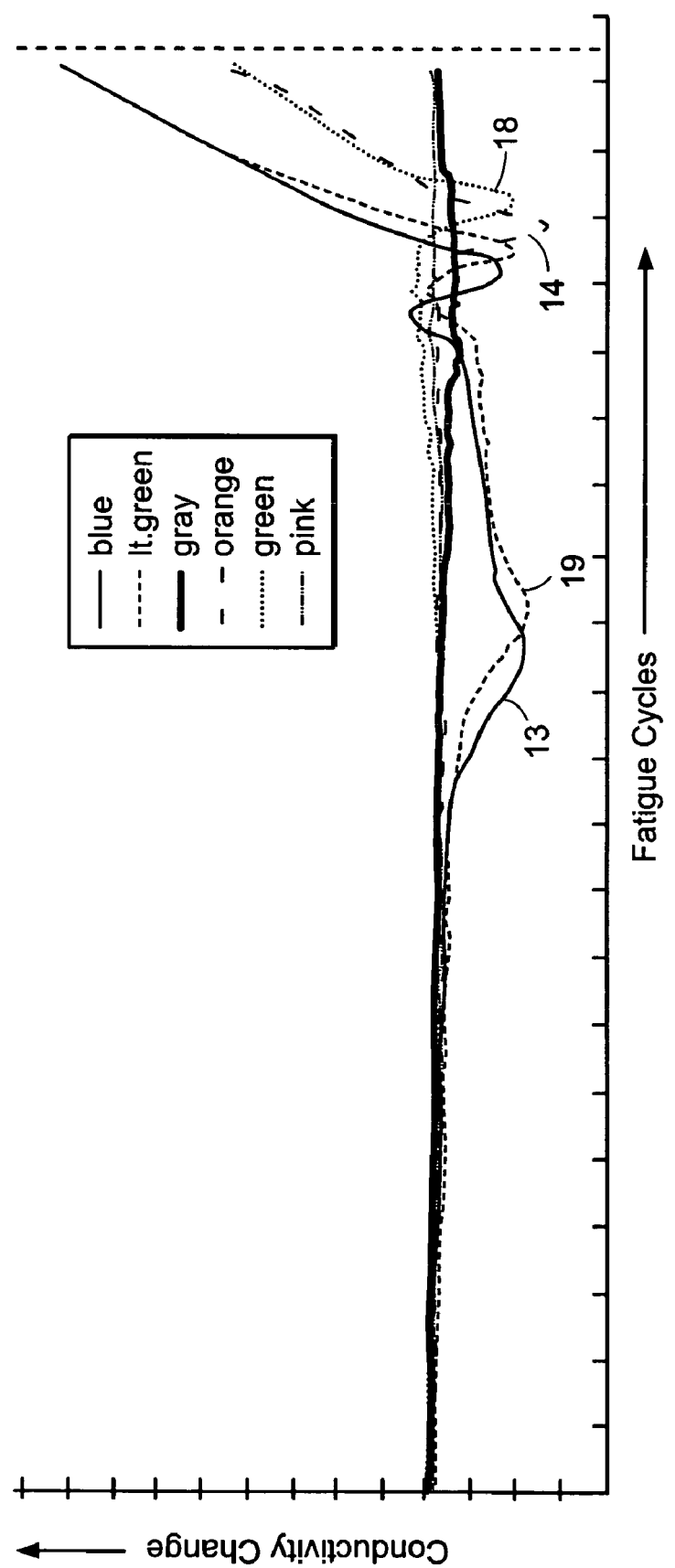
FIG. 19 illustrates the effective conductivity variation for a linear sensor array mounted between a pair of holes in a fatigue test specimen.

FIGS. 18 and 19 illustrates a representative set of data for the sensor array mounted over the ligament between the holes in the test row of an aluminum specimen. The numbers indicate the channel numbers of the array elements. The sense element response has been monitored while the part has been cyclically loaded at constant amplitude, but similar results have been obtained with variable or spectrum loading. As the number of fatigue cycles increases, the response of each sense element goes through a characteristic change as the crack reaches and then propagates across each sense element. The effective lift-off shows a small dip when the crack reaches the sense element, increases as the crack propagates across the element, and has another dip as the crack reaches the opposite side of the sense element. The lift-off continues to increases once the crack tip has extended into the next sense element, probably because of the greater compliance or crack opening that occurs during the loading cycle as the crack becomes longer. Similarly, variations hold for the effective conductivity response. Here the embedded MWM-Arrays proved to be durable enough to outlast the fatigue specimen. Individual tests have been run as long as 38,000 cycles with such embedded sensor array networks. Sensor arrays have also been reused.

The MWM-Array configurations can be surface mounted on a part. This mounting can take the form of a clamp or pressure fitting against the surface, or the sensors can be mounted with an adhesive and covered with a sealant. Because the MWM sensors do not require an intimate mechanical bond, compliant adhesives can be used to improve durability. The sensors may also be embedded between layers of a structure, such as between layers of a lap joint or under repairs using composites or metal doublers, possibly with a sealant or other fillers to support compressive loads.

The MWM sensors can also be packaged on a roll of adhesive tape. Individual lengths of the tape may be cut to meet the length requirements of particular application. For example, a single strip of tape containing numerous MWM-Rosettes may be placed along a row of fasteners relatively rapidly. Electrical connections can be made to bond pads for the individual sensors or groups of sensors. When mounted against a surface, the adhesive can be provided along one surface of the supporting membrane to bond the selected length of the sensor array to a part to be tested. When mounted between layers, the adhesive can be provided along both the upper and lower exposed surfaces.

The sensor can be covered with a top coat of sealant to provide protection from any hazardous environments, because processing of the measured responses through the measurement grids provides the capability for each sensing element to be individually lift-off compensated and access to each element is not required for calibration. Furthermore, the sensor can intentionally be set off a surface, or fabricated with a porous (or liberally perforated) substrate material, to avoid or minimize interference with the environment causing the corrosion process to occur on the surface and to provide continuous monitoring and inspection for stress corrosion cracking or corrosion fatigue.

Figure 20:
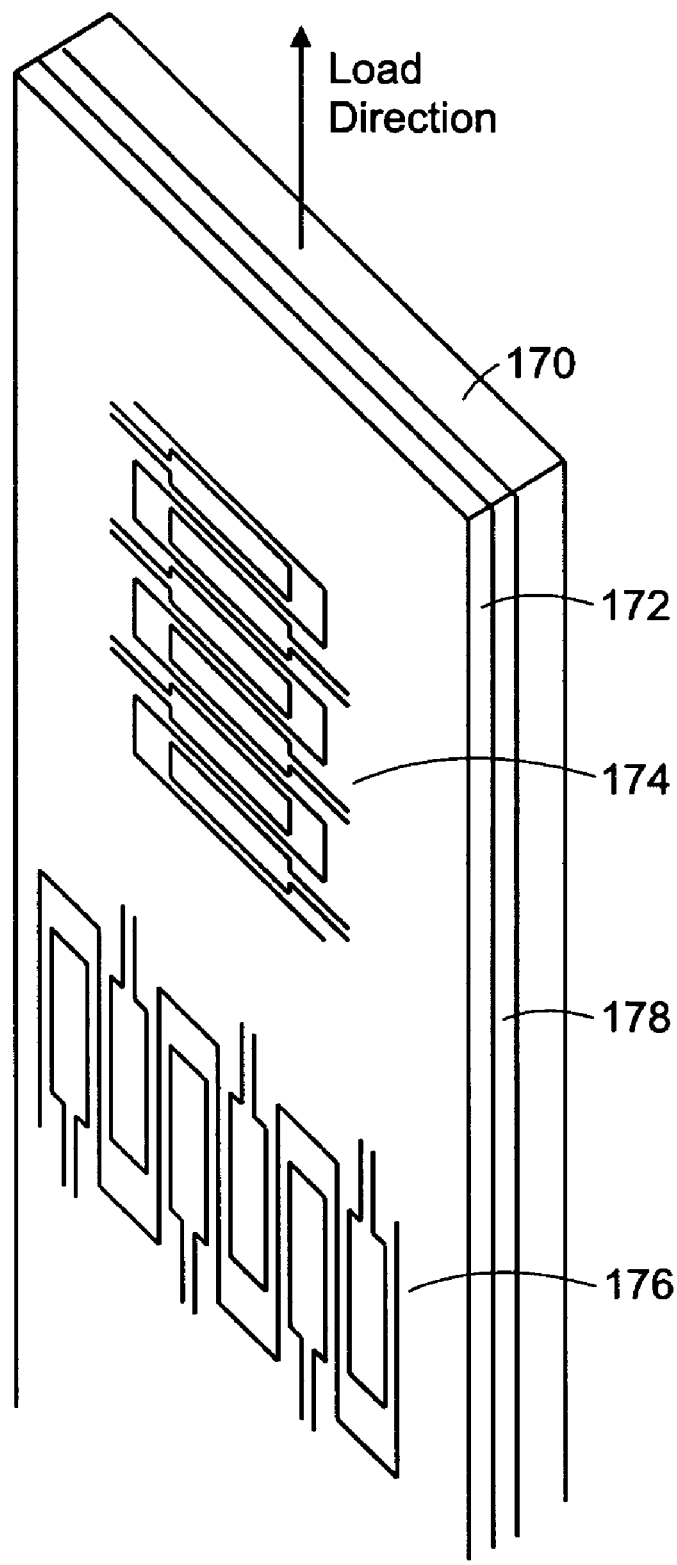
FIG. 20 is a schematic drawing of two MWM-Arrays mounted to a coated test material surface and oriented in different directions relative to the load direction.

FIG. 20 shows an example measurement configuration. The substrate material 170 can be a flat or curved steel component that may also have a protective cadmium coating 172. The MWM-Array 174 is oriented so that the relative permeability measurements will be sensitive to the applied stress or load. The MWM-Array 176 is oriented so that the relative permeability measurements will be insensitive to the applied stress or load. If an overload event occurs than the residual stress distribution will change and the response of all of the sense elements may be altered. In particular, the non-load sensitive sense elements may shift due to the different residual stress distribution. Note that if the substrate material 170 is a nonmagnetic material such as an aluminum alloy or a brass, then the coating 172 can be a thin magnetizable coating, such as a cobalt coating 0.015 mm (0.0006 in.) thick. Then the sensor arrays will be sensitive to the permeability changes in the coating, which reflect the stress of the substrate. The coating does not need to cover the entire component and only needs to be in the area being sensed by the sensor. A second coating 178 or a third material may also be added, to the front or back surface of the test material. The different materials may also be sensitive to different properties. For example, one layer may be more sensitive to stress while the other layer is more sensitive to temperature. Clearly, more materials could also be added.

To support probability of detection and other performance studies, similar methods can be used to fabricate a matrix of samples where the material conditions span a range of values. This range can provide significant value in assessing true NDI performance because real flaws are being used in the evaluation. In one embodiment of the invention, samples are fabricated under the same conditions, including the same predetermined material condition level, to build a probability density function to relate the sensor response to the uncertainty distribution for the material condition. For example, the probability density function may relate the crack signal to the crack size. These probability density functions or uncertainties can then be used to assess the capability to predict other dependent responses, such as the remaining life for the material. In another embodiment of the invention, the matrix contains multiple predetermined material condition levels where the processing of the specimen is to be stopped. For example, the samples may be fatigued and the fatigue processing is stopped for various crack sizes. This can be extended even further by preconditioning the samples differently, such as to different shot peen intensity levels, so a broader range of material states are under consideration. The matrix of samples can be used as for training the response of the sensors or as a test set for evaluation and validation of different sensing methods. For test sets, in order to provide a statistical basis for the studies such as probability of detection studies, the distribution of the damage states, such as crack sizes, is selected prior to processing and fabrication of the samples.

While the inventions have been particularly shown and described with reference to preferred embodiments thereof, it will be understood to those skilled in the art that various changes in form and details may be made therein without departing from the spirit and scope of the invention as defined by the appended claims.

All U.S. patents and patent applications mentioned above are incorporated herein by reference in their entirety. Additional reference incorporated by reference in its entirety:

Auld, B. A. and Moulder, J. C. (1999), "Review of Advances in Quantitative Eddy-Current Nondestructive Evaluation," Journal of Nondestructive Evaluation, vol. 18, No. 1.

What is claimed is:

1. A method for fabricating a sample with a predetermined material condition, said method comprising:
   placing a sensor proximate to a sample material surface;
   processing the material to alter the material condition;
   measuring a response with the sensor, with the sensor being proximate to the material surface for substantial periods to monitor progression of the material condition; and
   using a predetermined correlation between the sensor response and the material condition to stop processing the material when the material condition reaches a predetermined level.

2. The method as claimed in claim 1 wherein the sensor is an eddy current sensor.

3. The method as claimed in claim 1 wherein the sensor is an eddy current sensor array.

4. The method as claimed in claim 1 wherein the sensor conforms to the material surface shape.

5. The method as claimed in claim 1 wherein processing the material comprises fatiguing the material.

6. The method as claimed in claim 1 wherein the material condition is fatigue damage.

7. The method as claimed in claim 6 wherein the fatigue damage is a crack.

8. The method as claimed in claim 1 wherein processing the material comprises mechanical loading.

9. The method as claimed in claim 1 wherein processing the material comprises thermal loading.

10. The method as claimed in claim 1 wherein processing the material comprises combined mechanical and thermal loading.

11. The method as claimed in claim 1 wherein the material condition is residual stress.

12. The method as claimed in claim 1 wherein the material condition is thermal damage.

13. The method as claimed in claim 1 wherein the material condition is a subsurface flaw.

14. The method as claimed in claim 1 wherein the sample is representative of a complex aircraft component.

15. The method as claimed in claim 14 wherein the aircraft component has a coating.

16. The method as claimed in claim 1 wherein the sample is a component and processing the material comprises service aging.

17. The method as claimed in claim 1 wherein the sample material is artificially aged.

18. The method as claimed in claim 1 further comprising:
   preconditioning the material prior to processing.

19. The method as claimed in claim 18 wherein preconditioning comprises heat treating.

20. The method as claimed in claim 18 wherein preconditioning comprises shot peening.

21. The method as claimed in claim 1 further comprising converting the sensor response into an effective property.

22. The method as claimed in claim 21 wherein the effective property is electrical conductivity.

23. The method as claimed in claim 21 wherein the effective property is magnetic permeability.

24. The method as claimed in claim 21 wherein the effective property is lift-off.

25. The method as claimed in claim 21 wherein the effective property is a layer thickness.

26. The method as claimed in claim 21 wherein the effective property is an estimated damage state.

27. The method as claimed in claim 26 wherein the damage state is a flaw dimension.

28. The method as claimed in claim 1 wherein the predetermined correlation is determined empirically.

29. The method as claimed in claim 1 wherein the predetermined correlation is determined by a model.

30. The method as claimed in claim 1 wherein the material condition is the presence of a crack and the predetermined level is crack size.

31. A method for fabricating a matrix of samples having predetermined material conditions, said method comprising:
   a) placing a sensor proximate to a sample material surface;
   b) processing the material to alter a material condition;
   c) measuring a sensor response, the sensor being proximate to the material surface for substantial periods to monitor progression of the material condition;
   d) using a predetermined correlation between the sensor response and the material condition to stop the processing when the material condition reaches a predetermined level; and
   e) repeating steps (a)–(d) to create the matrix containing multiple samples.

32. The method as claimed in claim 31 wherein the processing comprises fatiguing.

33. The method as claimed in claim 31 wherein the multiple samples are fabricated with the same predetermined level for material condition to construct a probability density function to assess an uncertainty distribution.

34. The method as claimed in claim 33 further comprising:

using the probability density function to assess a capability to predict remaining life.

35. The method as claimed in claim 31 further comprising:
changing the predetermined level for material condition for at least one sample so that the matrix has multiple samples having different predetermined material condition levels.

36. The method as claimed in claim 31 further comprising:
preconditioning the material prior to processing, with at least one sample in the matrix having different preconditioning than another sample.

37. The method as claimed in claim 36 wherein preconditioning comprises shot peening.

38. The method as claimed in claim 31 further comprising:
using the matrix of samples as a training set.

39. The method as claimed in claim 31 further comprising:
using the matrix of samples as a test set.

40. The method as claimed in claim 39 wherein the test set is designed to support a probability of detection study.

* * * * *